(12) United States Patent
McGregor et al.

(10) Patent No.: US 8,898,022 B2
(45) Date of Patent: Nov. 25, 2014

(54) METHOD, SYSTEM AND DEVICE FOR ENHANCING FLOW FIELD DATA

(75) Inventors: Robert McGregor, Zurich (CH); Dominik Szczerba, Oetwil am See (CH); Gabor Szekely, Zurich (CH); Krishnamurthy Muralidhar, UP Kanpur (IN)

(73) Assignees: ETH Zurich, Zurich (CH); Indian Institute of Technology Kanpur, Kanpur (IN)

( * ) Notice: Subject to any disclaimer, the term of this patent is extended or adjusted under 35 U.S.C. 154(b) by 948 days.

(21) Appl. No.: 13/059,328

(22) PCT Filed: Aug. 25, 2008

(86) PCT No.: PCT/EP2008/061078
§ 371 (c)(1),
(2), (4) Date: Feb. 16, 2011

(87) PCT Pub. No.: WO2010/022762
PCT Pub. Date: Mar. 4, 2010

(65) Prior Publication Data
US 2011/0144920 A1    Jun. 16, 2011

(51) Int. Cl.
*G06F 19/00* (2011.01)
*G06F 17/50* (2006.01)

(52) U.S. Cl.
CPC ........ *G06F 17/5009* (2013.01); *G06F 2217/16* (2013.01); *G06F 19/3437* (2013.01)
USPC ......................................................... 702/19

(58) Field of Classification Search
CPC .... A61B 5/1455; A01N 1/0284; C12N 5/061; C12N 5/0612; C12Q 1/02
USPC .......................................... 702/19, 182–185
See application file for complete search history.

(56) References Cited

PUBLICATIONS

Boris, "The Threat of Chemical and Biological Terrorism: Preparing a Response," *Computing in Science and Engineering*, 2002, vol. 4, No. 2, pp. 22-32.
Yakhot et al., "A Reconstruction Method for Gappy and Noisy Arterial Flow Data," *IEEE Transactions on Medical Imaging*, 2007, vol. 26, No. 12, pp. 1681-1697.
Cenedese et al., "A laboratory investigation of the flow in the left ventricle of a human heart with prosthetic, tilting-disk valves," *Experiments in Fluids*, 2005, vol. 39, pp. 322-335.
Steinman, "Image-Based Computational Fluid Dynamics Modeling in Realistic Arterial Geometries," Annals of Biomedical Engineering, 2002, vol. 30, pp. 483-497.
McGregor et al., "Exploring the Use of Proper Orthogonal Decomposition for Enhancing Blood Flow Images Via Computational Fluid Dynamics," *MICCAI*, 2008, vol. 5242, pp. 782-789.
Anttonen et al., "Applications of Multi-POD to a Pitching and Plunging Airfoil," *Mathematical and Computer Modelling*, 2005, vol. 42, pp. 245-259.
International Search Report in International Application No. PCT/EP2008/061078; dated Dec. 2, 2010.
Written Opinion of International Searching Authority in International Application No. PCT/EP2008/061078; dated Dec. 2, 2010.

*Primary Examiner* — Edward Raymond
(74) *Attorney, Agent, or Firm* — Oliff PLC

(57) ABSTRACT

A method, system and device are described for generating high-resolution flow-field data from sparse measurement data by interpolating from a reference database of pre-computed, highly-resolved fluid dynamic simulation results, to generate a highly-resolved set of flow field data which correspond to the sparse measurements. In one embodiment, the method, system and device use Principal Component Analysis techniques to interpolate the multidimensional fluid flow data. Applications of the invention are, amongst others, in the field of biomedical diagnosis involving fluid dynamic modeling of biological fluid systems such as blood flow in an artery.

15 Claims, 2 Drawing Sheets

METHOD, SYSTEM AND DEVICE FOR ENHANCING FLOW FIELD DATA

The present invention relates to the field of flow simulation and analysis in fluid systems, and in particular to the generation of high-resolution flow field data from sparse measurement data. Embodiments of the invention are also described with reference to their application in the field of biomedical diagnosis involving fluid dynamic modeling of biological fluid systems such as blood flow in an artery or airflow in a trachea.

DESCRIPTION OF THE PRIOR ART

In modeling the flow characteristics of a fluid system, it is known to generate high-resolution flow field data by performing detailed computational fluid dynamic (CFD) simulations using a set of input parameters for the given system-boundary conditions such as flow velocity, or pressure at the inlet and/or outlet, physical properties such as density, viscosity or fluid temperature, as well as geometrical information about features which may affect the flow simulation, such as the physical dimensions of enclosing walls or obstructions, or the texture or elasticity of surfaces affecting the fluid flow. Such input parameters may be measured and moreover such measurements may also be made over many time intervals in order to give a temporal dimension to the input of the simulation.

In the field of clinical diagnosis, such as in the analysis of vascular diseases, it is vital to know as much as possible about the blood flow in critical parts of the vascular system. For instance, information about localized pressure or wall shear stress (WSS) on parts of the wall of arteries can help in anticipating the onset of conditions such as aneurysms, which can be potentially fatal in the case of their rupture. Atherosclerosis and coronary heart disease are life-threatening conditions which also can be better investigated and understood, in particular in the light of knowledge of the specific hemodynamic conditions. Systems exist which attempt to measure patient-specific blood flows in a clinical setting, such as Phase Contrast Magnetic Resonance Imaging (PC-MRI) or Doppler ultrasound. These imaging systems produce coarse and noisy velocimetric data representing the fluid flow across a region of interest, and the measurements typically suffer from a low signal-noise ratio, especially at low flow velocities, so there is a need to enhance the data to reduce the effect of noise and to improve the resolution at specific locations of interest.

To overcome these limitations it has been proposed to use computational fluid dynamics in conjunction with medical imaging so as to obtain highly resolved time-dependant flow fields. Such an approach is described in an article by D. A. Steinman entitled "Image-based computational fluid dynamics modeling in realistic arterial geometries" and published in the Annals of Biomedical Engineering Volume 30, Number 4 (April 2002), pages 483-497. This presents many advantages as it gives access to a wealth of data, not only velocity but also pressure distributions as well as secondary flow properties, such as WSS, which can easily be found by post-processing. Unfortunately this also has the disadvantage of requiring large computational effort to calculate these flow solutions, thus limiting the application of these technologies in the clinical setting where powerful computing facilities may not be available and where the CFD results may be required urgently. In some cases, simulation times can run into hours, days or weeks, even if using high-performance computers with dedicated software and optimized hardware architectures. In addition, running such simulations requires trained personnel with considerable CFD know-how, thus adding a new member to the clinical team. Performing such high resolution simulation is therefore hardly practicable in a clinical environment. In order to provide patients with appropriate treatment, clinicians often need hemodynamic analysis information within a much shorter time than it would take to perform such detailed simulations.

Another drawback of this approach is that it does not make much use of the flow measurements which are eventually available. Typically the only flow information which is taken into account is the mass flow rate at the inlets and outlets. At best, the flow velocity distribution at the inlet and mass flow at the outlet may be used. At worst, an assumed flow waveform is used as an approximation for a patient-specific geometry. However, using the mass flow rate and a generic inflow velocity distribution completely ignores the effect of upstream disturbances and using a velocity field directly from the measurement means that any measurement error will be carried over into the simulation and will thus give rise to significant errors in the high-resolution flow field data generated.

It is therefore an objective of the preferred embodiments of the present invention to provide a system and method of generating high-resolution flow field data which can produce results quickly, and which can use all of the available diagnostic information. In particular, the preferred embodiments include a method as set out in claim 1, a system as set out in claim 8, a device as set out in claim 11 and a method as set out in claim 12. Further embodiments of the present invention are also set out in the appended claims.

DETAILED DESCRIPTION OF THE INVENTION

Figure 1:
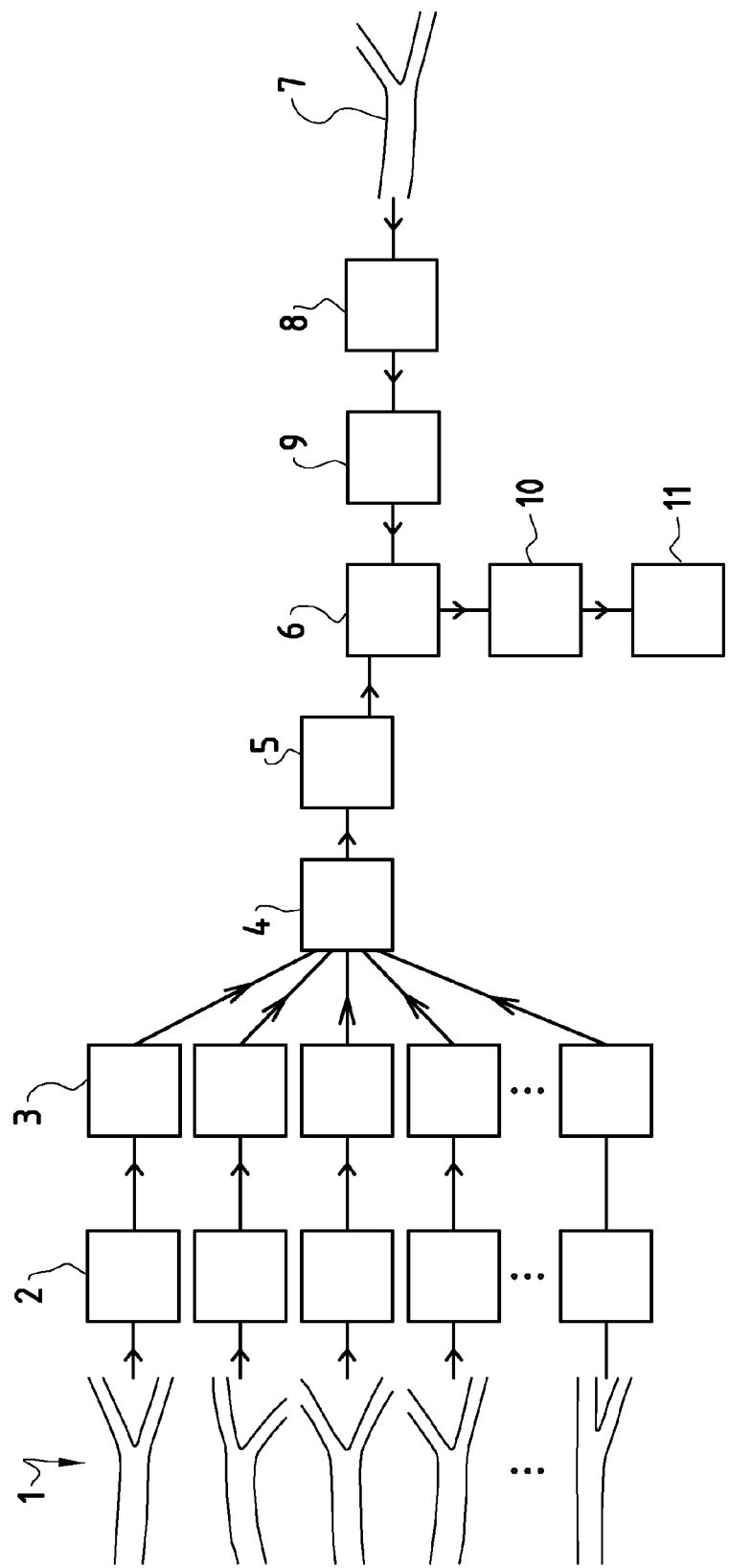
FIG. 1 is an illustration of a method in accordance with an embodiment.

The present invention will be described with reference to the attached drawing, FIG. 1. In the following description, references to specific applications of the invention, for example to the modeling of blood flow in human blood vessels, are given by way of example only, and should not be interpreted as limiting the scope of the invention, which is applicable across a broad range of fluid systems analysis. The particular example of blood flow in the abdominal aortic bifurcation is used to illustrate the method of the invention. Knowledge of the hemodynamic conditions in the abdominal aortic bifurcation is of significant medical relevance as it is a determining factor in the pathogenesis of abdominal aortic aneurysms, a leading cause of death in developed countries.

As mentioned above, it is possible to use CFD techniques to generate high-resolution flow-field data for fluid dynamic analysis purposes, for example in the diagnosis of vascular disease. However, currently available methods involve performing CFD simulations which require extensive computing power and may take days, or even weeks, to run. The present invention relies upon the idea of performing computer-intensive simulations in advance for a range of reference situations and then using the high-resolution flow field data generated in these simulations to efficiently calculate a new set of high resolution flow field data for the patient-specific set of parameters. In this way it is possible to generate accurate and high-resolution flow field estimates for the patient-specific case, but without actually performing a patient-specific CFD simulation.

All the simulation work is done beforehand, and accumulated in a reference database which represents knowledge of the flow patterns typically occurring at a given vascular location. This is then used to perform an intelligent interpolation, based on the measurement data, to arrive at a set of highly-resolved flow field data for the specific location of the specific blood vessel in the specific patient.

The key to the method is a database of trusted solutions. These can come from patient-specific simulations for a representative sample of similar vascular geometries, although appropriate analysis techniques also allow larger reference databases to be used, containing more disparate samples, without degrading the quality of the patient-specific result.

The CFD simulations which produce the flow field data in the reference database may be performed by known CFD techniques, for example using a Finite Element Method to solve the incompressible Navier-Stokes equations for each of the reference fluid systems. The more reference systems there are in the reference database which are similar to the patient-specific system, the more accurate will be the flow field data for the patient-specific case. And the more varied the range of reference fluid systems, the broader will be the range of patient-specific cases where the reference database can be used to produce accurate results.

An embodiment of the method of the invention is shown schematically in FIG. 1, using as an example the fluid flow through a bifurcation of a patient's blood vessel (7). In FIG. 1, the process of creating a reference database from the reference samples (1) is set out schematically in steps 2 to 5. The capture and pre-processing of the data from a patient's blood vessel (7) takes place in steps 8 and 9, and the interpolation and post-processing takes place in steps 6, 10 and 11.

The reference database of CFD simulation results can be created as follows:

So as to perform a large number of simulations, many sets of parameters need to be measured or estimated at the location of interest (1). These may be any parameters which can be used as boundary conditions or physical properties needed for performing CFD fluid flow simulations, including for example: patient-specific geometry, inflow velocity profiles, wall displacements, pressure at inflow/outflow, blood viscosity or wall elasticity. They may be real measurements taken from many real patients, or they may be derived in other ways, for example by estimating or computer-modeling based on assumptions about real patients. Using these parameters as input, flow simulations are performed thus recovering the highly-resolved flow fields (2) as well as all the associated information, such as the pressure fields, WSS distributions or wall deformations. All this information is put into the reference database (4). Additionally, any further information helping to characterize the individual cases can also be measured or estimated and appended to the already rich flow field information—for example, in the case of a bifurcation, it may be useful to include parameters indicating the degree of flow symmetry across the inlet or between the two branches, or the branching angles or relative cross-sectional areas of the various parts of the geometry.

This process of data gathering and simulation can be very lengthy, but once the database has reached a sufficient size, it can already be used to perform flow field estimation. The data gathering and simulation may still be continued in parallel to further extend the database and thus increase the span of cases that can be covered and improve the achievable accuracy of the method.

In order to make the reference simulations comparable a common coordinate system is needed. This normalization step is shown as step 3 in FIG. 1. The geometric coordinates of the blood vessel may be normalized to a standard reference coordinate system, such as a volume mesh, and the bifurcation geometries in the reference database can then be redefined in terms of this standard coordinate mesh. In the example of the aortic bifurcation, the left and right branches can be described in terms of a variation in take-off angles, or in terms of the extent to which the curvature of a wall section varies from the curvature of the corresponding wall section in the reference mesh. For the flow velocity vector components of the various reference samples to be comparable, these also need to be mapped onto a common coordinate system, and a similar operation can be performed to normalize the spatial and temporal parameters of these vector data.

Once the database (4) has been filled with many highly-resolved flow simulations which have all been normalized so as to be directly comparable (3), one may begin using the method of this invention to efficiently estimate highly-resolved patient-specific flow fields in a clinical setting.

The efficient estimation of patient-specific flow fields can be done as follows:

Patient-specific predictor parameters are measured (8) for the blood vessel (7) at the location of interest. These predictors may be any type of information which is stored in the database. For example, PC-MRI allows three-dimensional flow field measurements to be taken at various points in the geometry at predetermined time intervals, giving a specific but sparse set of data characterizing the flow through the bifurcation of the blood vessel. So one could for example use these velocity measurements as predictors. The associated geometric parameters, which may also be retrieved from the MRI measurement, may also be used as such.

These predictor parameters are normalized (9) to adjust the spatial and/or temporal coordinates of the geometry under investigation so that they map onto the coordinate systems used for normalizing the reference simulation input data.

Once the predictor data have been normalized (9) an interpolation (6) is performed on the data stored in the reference database (4), to determine a combination of reference cases which best corresponds to the predictor parameter data for the given patient.

A particularly efficient interpolation method according to one embodiment of the invention uses a Principal Component Analysis (PCA) technique. Basically a PCA of the reference database is performed (5), which de-correlates the data and stores it in eigenmodes, rather than individual cases. Each data set (covering all collected information including simulation results) can then be expressed as a linear recombination of these eigenmodes. The interpolation then becomes a search for the linear combination of eigenmodes which delivers the set of interpolated predictors which best matches the set of measured predictors. This can be formulated as an optimization problem. Once the optimal weightings for each eigenmode have been found, the full flow field data can be recovered by performing the linear combination using these weightings (6).

Once this interpolation has been performed the resulting flow field data are still normalized and need to be mapped back (10) to the original configuration.

The flow field data thus obtained (11) should represent the high resolution flow field data which would have been obtained by directly performing a CFD simulation on the measured patient-specific data. In this way, the CFD solutions can be used to reconstruct the fine detail of a patient-specific flow field, without actually performing a simulation. This has the added advantage of using a maximal amount of the measured information.

As the mathematical interpolation operation is based on optimization, the goal function may be adapted to include cost terms which can be used to reduce the effects of noise in the patient-specific data by diminishing the strength of the constraints imposed by each measured value. In this embodiment of the invention, the interpolation is done by performing an optimization, which is an over-determined fitting problem. In this case, reliability of the measurements could be taken into account by building a goal-function for the optimization which incorporates the relative measurement noise.

References are made in this application to Principal Component Analysis (PCA). However, it should be understood that this mathematical vector transform operation has several other names in various contexts, such as Singular Value Decomposition, Proper Orthogonal Decomposition or Karhunen-Loève transform, and that the term PCA can be used interchangeably with these.

Example Application of the Invention

In the example given, the invention is used for obtaining high resolution patient-specific abdominal aortic flow fields from PC-MRI data. It is emphasized that this is an example of one of the many applications of the present invention and in no way limits the invention to this application. It is also noted that the term "fluid" used in this application should be understood in its literal sense, such that it can refer to a gas, a liquid, a plasma, or indeed anything which is capable of flowing.

In the example application, the abdominal aortic bifurcation is the branching at which the abdominal aorta coming from the heart splits into the two common iliac arteries which supply blood to the legs. It is a common location for atherosclerosis, a disease caused by the deposition of plaques in the arteries. Abdominal aortic aneurysms, a progressive enlargement of the abdominal aorta which can eventually rupture and lead to death, is another disease which also occurs at this location. Both these diseases are increasingly common in developed countries, and their pathogenesis is believed to be linked to the blood flow patterns in the abdominal aortic bifurcation. It would therefore be of interest to physicians to have tools which would allow for estimating these patterns in-vivo. One of the applications of the present invention is in enabling such diagnostic procedures to be performed.

Generating the Set of Reference Simulations

As shown in FIG. 1, step 1 is to build a database with many different reference cases. In this case it is done by acquiring many different patient-specific abdominal aortic bifurcation geometries. These may be acquired using Computed Tomography (CT) scans, for example, so as to obtain high quality, isotropic images of the reference patients' abdomens (1). These images must then be segmented, so as to recover the geometry of the abdominal aortic bifurcation. Once this has been done a skeleton model can be extracted, which will later be used for mapping onto the reference geometry. Using the segmented images, computational meshes can be generated which will be used for the simulations.

Once the meshes have been generated, boundary conditions are still needed for the flow simulations. So as to obtain realistic boundary conditions, Doppler velocimetry ultrasound measurements are performed on the reference patients, proximal to the bifurcation. These will enable an estimate to be made of the mass flow rate at all phases of the cardiac cycle. This information can be used to generate an assumed time-dependent parabolic inflow velocity profile which respects the measured mass flow rates. This is imposed as inflow boundary condition, and a zero pressure condition is imposed at both outflows, thereby ensuring well-posed boundary conditions for the system of partial differential equations. The Navier-Stokes equations are then solved numerically for several heart cycles, thus delivering a high resolution, time-resolved flow field for each of the measured geometries (2). The solution of the Navier-Stokes equations represents in the case the performing of a CFD simulation.

Figure 2:
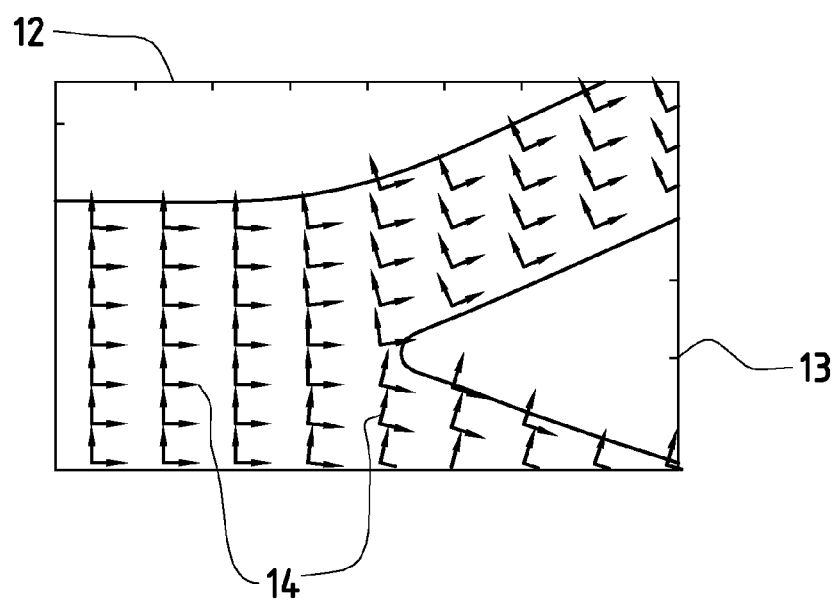
FIG. 2 is an illustration of a coordinate transform in accordance with an embodiment.

These simulations still need to be mapped onto a reference mesh before they can be added to the reference set. The reference geometry in this case is a generic bifurcation with straight segments and left and right bifurcation angles of 23°, which corresponds approximately to the mean of the observed bifurcation angles. The mapping is done via the skeleton models by transforming both the anatomy and the velocities into a locally adapted, skeleton-based coordinate system from the original, global Cartesian frame. Such a coordinate transform is illustrated in 2D in FIG. 2, which shows a regular orthogonal coordinate system of coordinates (12, 13), each point in the coordinate system showing its local body-fitting coordinate axes (14). Thus every node of the simulation mesh can be mapped to an equivalent position on the reference geometry. Once this coordinate transformation has been performed (3), the simulation results are ready to be added to the reference set (4). Note that, while FIG. 2 shows a two-dimensional vector field, it should be understood that in practice the system may have many dimensions, including, for example, three velocity components, pressure, fluid density and any other parameter which may be found to be useful to measure at the point in question. Note also that the orthogonal coordinate system of FIG. 2 is just for illustration purposes. In practice, a more complex reference mesh may be required, such as a tetrahedron-based volume mesh which may also vary in scale, depending on the geometry being represented, for example, such that the mesh is finer near points of the geometry which require more highly-resolved simulation data, and coarser at points in the geometry where a lower resolution is required.

Each set of simulation results (for example velocities and pressures at each point at each time) is organized into a single vector and added to all the other simulation results to form a large two-dimensional matrix. This way of storing the data, in its transformed state, makes performing the PCA easier, and reduces the number of processing operations, and hence the amount of time and the complexity of the equipment, required to use the reference data in a clinical setting.

Measuring a Patient-Specific Flow Field

Now that the reference data set is available, one is able to perform an actual flow field measurement on a patient using the present invention's method. In this case, this will be done based on PC-MRI images of the patient's abdominal aorta (7). The PC-MRI data provides four time-resolved data volumes (8). One will contain anatomical information and the other three will be the individual components of the velocity vectors. The anatomical data volume is used to recover the geometric information by first segmenting the artery's lumen and then using the resulting binary mask to generate a skeleton consisting of the vessel's midline. The segmentation and skeleton model are then used to map the measured velocity information back to the reference geometry, so that it is expressed in the same terms as the reference data set (9).

However the velocity information from the PC-MRI measurement for the patient will be much sparser than the velocity information contained in the reference data set. Each reference simulation is stored as a vector of size M, and the measured velocity information is organized in the same way as a vector r of length N, where M is much larger than N. The relation of the sparse measurement data to the dense reference data can be expressed by a vector L of length M which has the value 1 for each of the reference data values which one was able to measure, and 0 elsewhere, so that L has N non-zeros. The full reference set is the two-dimensional matrix X, which has the dimensions M×K, where K is the number of reference simulations that are in the database.

The goal is now to find x, the full solution vector of length M which contains Lx, the reduced solution vector of size N which best matches r, the vector representing the measurement data. By performing a PCA (5) on X, the 2-dimensional matrix containing all the reference simulation data, one obtains a set of de-correlated eigenvectors V, which can be linearly combined to recreate any of the reference flow fields in the database as well as new flow fields which will be an interpolation of these reference simulations. So as to find the linear combination of eigenvectors which best fits the measured data, one performs an optimization operation. A goal function is defined to drive this over-constrained optimization problem in the form of a weighted sum of the squared deviation between the components of the solution vector Lx and the measurement vector r, in order to minimize the global deviation between Lx and r. The weights are selected to be proportional to the signal-to-noise ratio of the individual measurements, in order to relax the enforced constraints where available data are less reliable and therefore restrict the influence of measurement errors on the final solution. Once the goal function has been formulated, the optimization may be performed using any minimization strategy which can find its optimum. This will result in a set of coefficients which can then be used to obtain the final highly resolved flow field as a linear combination of the full eigenvectors.

Once this highly resolved flow field is available (6), it still needs to be mapped back from the reference geometry to the original geometry. This can easily be done by using the skeleton model to perform an inverse coordinate transform, back into the original Cartesian coordinate system (10). This results in the final, highly resolved flow field (11) data which represent the simulation results which would have resulted from a set of boundary conditions similar to the measured, patient-specific parameter data.

The invention claimed is:

1. Method of obtaining highly resolved flow field data representing the flow characteristics of fluid in a fluid system under analysis, comprising a first step of measuring and/or estimating parameters of the fluid system under analysis to produce a set of flow predictor parameters for the fluid system under analysis,
    the method comprising the further steps of,
    using a reference database containing highly resolved flow field data representing fluid flow simulation results of a reference set of fluid systems and flow predictor parameters of each of said set of reference fluid systems, performing a mathematical interpolation operation on said reference database to determine an interpolated set of flow predictor parameters, matching, to within predetermined error margins, the said set of flow predictor parameters of the fluid system under analysis, and
    determining, from said reference database, a set of highly resolved flow field data corresponding to the said interpolated set of flow predictor parameters.

2. Method according to claim 1, including the steps of performing a vector transform operation on the highly resolved flow field data and the flow predictor parameters in the database, and performing the mathematical interpolation on the transformed data.

3. Method according to claim 2, in which the vector transform operation is a Principal Component Analysis, a Factor Analysis or an Independent Component Analysis.

4. Method according to claim 1, in which the fluid system under analysis is a biological fluid flowing in a biological conduit.

5. Method according to claim 4, in which the fluid system under analysis is blood flowing through a branching geometry of a blood vessel.

6. Method according to claim 1, further comprising a normalizing step for mapping the measured and/or estimated flow predictor parameters for the fluid systems observed on to a common coordinate system used in the reference database.

7. Method according to claim 1, in which the step of measuring and/or estimating fluid flow parameters of the fluid system under analysis includes the steps of measuring and/or estimating fluid flow parameters of the fluid system under analysis at each of a plurality of time intervals, and in which the set of flow predictor parameters for the fluid system under analysis includes flow predictor parameters for each of said time intervals.

8. Method of producing a reference set of high resolution flow field vector data suitable for the method of claim 1, comprising the steps of, for each of a plurality of reference fluid systems,
    measuring and/or estimating fluid flow predictor parameters at each of a plurality of time intervals,
    performing high-resolution flow simulations using the said fluid flow predictor parameters, so as to thereby produce high-resolution flow field data descriptive of fluid flow in each of said reference fluid systems, and
    storing in a reference database the said fluid flow predictor parameters and said high-resolution flow field data produced by said high-resolution flow simulations.

9. Method according to claim 8, including the step of normalizing the fluid flow predictor parameters for the plurality of reference fluid systems so as to map the fluid flow predictor parameters on to a common set of coordinates at each of a plurality of time intervals.

10. Method according to claim 8, in which the step of storing in a reference database the said fluid flow predictor parameters and said high-resolution flow field data includes the step of performing a mathematical transform on the said fluid flow predictor parameters and the said high-resolution flow field data, such that the fluid flow predictor parameters and high-resolution flow field data are stored in the reference database as the results of the mathematical transform.

11. Method according to claim 8, in which the vector transform operation is a Principal Component Analysis, a Factor Analysis or an Independent Component Analysis.

12. System for obtaining highly resolved flow field data representing the flow characteristics of fluid in a fluid system under analysis, the system comprising:
    data capture means for capturing a set of flow predictor parameters for the fluid system under analysis from measured and/or estimated parameters of the fluid system under analysis,
    data retrieval means for retrieving, from a reference database, highly resolved flow field data representing fluid flow simulation results of a set of reference fluid systems and flow predictor parameters of each of said set of reference fluid systems,
    first calculation means for determining, by interpolation from said highly resolved flow field data and flow predictor parameters of said set of reference fluid systems, an interpolated set of flow predictor parameters which match, to within predetermined error margins, the said set of flow predictor parameters of the fluid system under analysis, and second calculation means for determining, from said reference database, a set of highly resolved flow field data which corresponds to the said interpolated set of flow predictor parameters.

13. System according to claim 12, in which the first calculation means include means for performing a mathematical vector transform operation on the highly resolved flow field data and the flow predictor parameters in the database, and means for performing an interpolation on the mathematically transformed highly resolved flow field data.

14. System according to claim 13, in which the vector transform operation is a Principal Component Analysis, a Factor Analysis or an Independent Component Analysis.

15. Medical diagnostic device for analyzing fluid flow characteristics of biological fluid flowing in a biological conduit of a patient, the device comprising diagnostic data capture means for acquiring parameters of the fluid flow through the biological conduit, and for generating therefrom a set of patient specific flow predictor parameters for the fluid flow through the biological conduit of the patient, data retrieval means for retrieving high resolution flow field data and corresponding flow predictor parameters from a reference database, interpolation means for, by interpolation of the high resolution flow field data and corresponding flow predictor parameters retrieved from the reference database, determining a set of interpolated flow predictor parameters which match, to within predetermined error margins, the said set of patient-specific flow predictor parameters, reference transform data, which best fit said diagnostic transform data, and second mathematical vector transform means for performing an inverse transform operation on said set of best-fit transform data, so as to produce a diagnostic set of high resolution flow field vector data corresponding to said diagnostic flow field vector data.

\* \* \* \* \*